United States Patent
Genuer et al.

(10) Patent No.: US 10,247,668 B2
(45) Date of Patent: Apr. 2, 2019

(54) SYSTEM FOR OBSERVING OBJECTS

(71) Applicant: Commissariat à l'énergie atomique et aux énergies alternatives, Paris (FR)

(72) Inventors: Valentin Genuer, Saint-Sauveur (FR); Pierre Marcoux, Saint Egreve (FR); Emmanuelle Schultz, Saint Egreve (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/536,526

(22) PCT Filed: Dec. 16, 2015

(86) PCT No.: PCT/EP2015/080106
§ 371 (c)(1),
(2) Date: Jun. 15, 2017

(87) PCT Pub. No.: WO2016/097063
PCT Pub. Date: Jun. 23, 2016

(65) Prior Publication Data
US 2017/0356846 A1  Dec. 14, 2017

(30) Foreign Application Priority Data
Dec. 17, 2014  (FR) .................................. 14 62645

(51) Int. Cl.
*G01N 21/47* (2006.01)
*G02B 21/00* (2006.01)
*G03H 1/04* (2006.01)

(52) U.S. Cl.
CPC ....... *G01N 21/474* (2013.01); *G01N 21/4788* (2013.01); *G02B 21/0092* (2013.01);
(Continued)

(58) Field of Classification Search
CPC ... G01N 21/47; G01N 21/4788; G01N 21/474
(Continued)

(56) References Cited

U.S. PATENT DOCUMENTS

| 4,492,467 A | 1/1985 | Drain et al. |
| 5,181,080 A * | 1/1993 | Fanton ................. G01B 11/065 356/128 |

(Continued)

FOREIGN PATENT DOCUMENTS

| FR | 3001544 | 8/2014 |
| WO | WO-0055669 | 9/2000 |
| WO | WO-0183673 | 11/2001 |

OTHER PUBLICATIONS

International Search Report for PCT/EP2015/080106, dated May 11, 2015.
(Continued)

*Primary Examiner* — Roy M Punnoose
(74) *Attorney, Agent, or Firm* — B. Aaron Schulman, Esq.; Stites & Harbison, PLLC

(57) ABSTRACT

A system is provided for observing objects on a substrate which includes a light source that emits polarized light rectilinearly along a first direction, a holder that receives said substrate having a surface and includes objects, wherein at least one of the holder or the substrate are translucent or opaque, a detector that collects the backscattered light from the interaction between the light emitting by the light source and the objects, a polarization splitter and a quarter-wave plate wherein the polarization splitter and the quarter-wave plate are arranged so that the polarization splitter directs light towards the substrate through the quarter-wave plate, and wherein the light forms a beam and the system modifies the size of the beam. The system thus allows one to observe objects on a non-transparent substrate.

16 Claims, 5 Drawing Sheets

Figure 1:
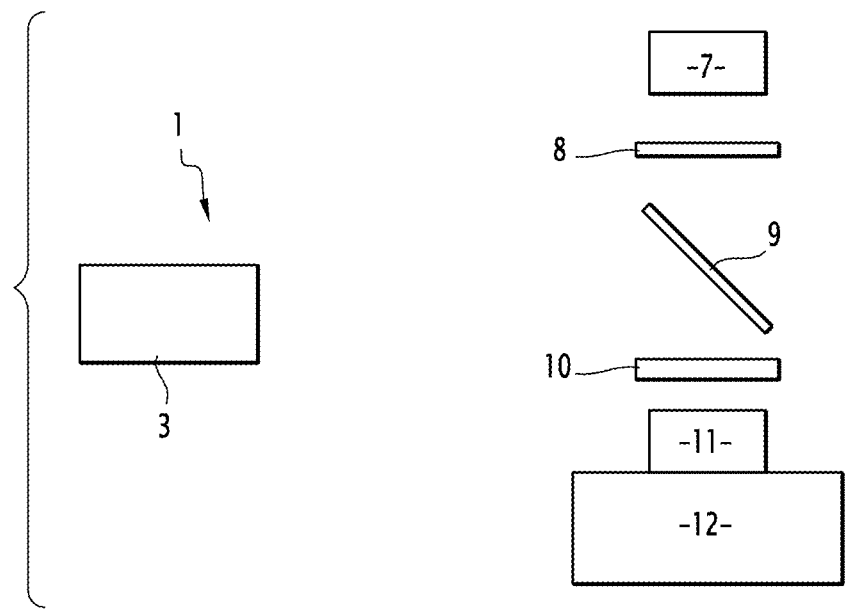

(52) U.S. Cl.
CPC ............ *G01N 2021/4792* (2013.01); *G03H 2001/045* (2013.01); *G03H 2001/0447* (2013.01); *G03H 2001/0452* (2013.01); *G03H 2001/0469* (2013.01); *G03H 2222/31* (2013.01); *G03H 2223/20* (2013.01)

(58) Field of Classification Search
USPC ...................................................... 356/446
See application file for complete search history.

(56) References Cited

U.S. PATENT DOCUMENTS

| | | | |
|---|---|---|---|
| 6,180,940 B1* | 1/2001 | Galstian | G21K 1/006 |
| | | | 250/251 |
| 6,720,547 B1* | 4/2004 | Rajadhyaksha | G01N 21/21 |
| | | | 250/208.1 |
| 7,317,540 B1* | 1/2008 | Kim | G01N 21/4795 |
| | | | 356/497 |
| 7,465,560 B2 | 12/2008 | Hirleman, Jr. et al. | |
| 8,310,681 B2* | 11/2012 | Hogan | A61B 5/0002 |
| | | | 356/497 |
| 8,748,122 B2 | 6/2014 | Hyman et al. | |
| 2005/0185192 A1* | 8/2005 | Kim | A61B 5/0066 |
| | | | 356/497 |
| 2006/0275847 A1 | 12/2006 | Goodyer et al. | |
| 2008/0310692 A1 | 12/2008 | Robinson et al. | |
| 2008/0317201 A1* | 12/2008 | Hogan | A61B 5/0002 |
| | | | 378/19 |
| 2011/0136165 A1 | 6/2011 | Vojnovic et al. | |
| 2014/0226158 A1 | 8/2014 | Trainer | |
| 2014/0303463 A1* | 10/2014 | Robinson | A61B 5/14552 |
| | | | 600/316 |

OTHER PUBLICATIONS

Written Opinion for PCT/EP2015/080106, dated May 11, 2016.
Preliminary Search Report for FR 1462645, completed Aug. 4, 2015.

* cited by examiner

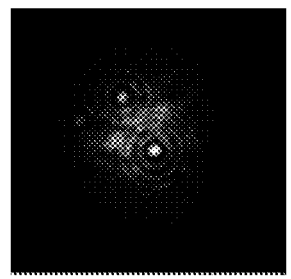
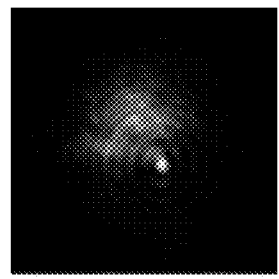
FIG.7  FIG.8
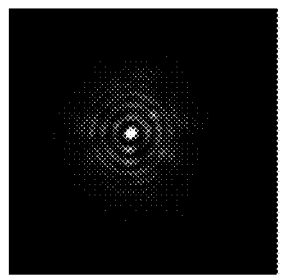
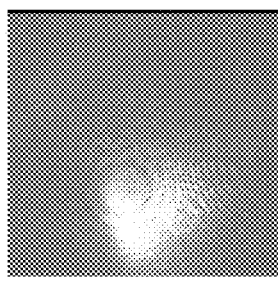
FIG.9  FIG.10
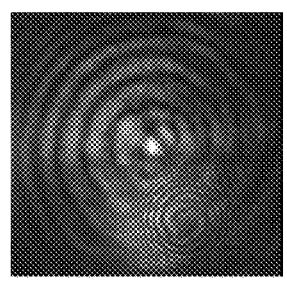
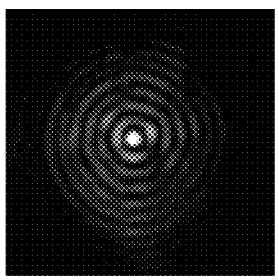
FIG.11  FIG.12

SYSTEM FOR OBSERVING OBJECTS

FIELD OF THE INVENTION

The present invention relates to a system for observing objects.

BACKGROUND OF THE INVENTION

It is known from documents US 2008/0310692 A1, U.S. Pat. No. 7,465,560 B2 and EP 2,122,326 B1 to determine the biological species of a bacterium by studying the transmission pattern obtained by the diffusion of incident photons by the bacteria, the bacterium being on a substrate.

However, such a transmission pattern cannot be obtained when the substrate includes blood, since the low transmission coefficient of blood prevents obtaining the diffraction pattern. Indeed, in the aforementioned documents, image obtainment in transmission does not work when the substrate and its holder are opaque.

SUMMARY OF THE INVENTION

There is therefore a need for a system for observing objects making it possible to observe the objects on a non-transparent substrate.

To that end, a system for observing objects is proposed including a light source able to emit polarized light rectilinearly along a first direction, a holder able to receive a substrate having a surface including objects, at least one of the holder and the substrate being translucent or opaque, a detector able to collect the backscattered light from the interaction between the light emitted by light source and the objects, a polarization splitter able to reflect polarized light rectilinearly along a second polarization direction and able to transmit polarized light rectilinearly along a third direction, the second polarization direction being perpendicular to the third direction, and a quarter-wave plate.

The splitter and the quarter-wave plate being arranged so that the splitter directs the light emitted by the light source toward the substrate and directs the backscattered light from the interaction between the light emitted by the light source and the objects toward the detector.

"Directing the light beam" means transmitting or reflecting the light beam.

Thus, according to a first embodiment, the splitter and the quarter-wave plate are arranged so that the splitter reflects the incident light relative to the splitter toward the substrate and transmits the backscattered light from the interaction between the light emitted by the light source and the objects toward the detector. According to another embodiment, the splitter and the quarter-wave plate are arranged so that the splitter transmits the incident light relative to the splitter toward the substrate and reflects the backscattered light from the interaction between the light emitted by the light source and the objects toward the detector.

According to specific embodiments, the system comprises one or more of the following features, considered alone or according to any technically possible combinations:
the objects are microorganisms, the substrate being a solid substrate, in particular an agar substrate, suitable for the growth of said microorganisms.
the first direction and the second direction are identical.
the first direction is different from the second direction, in which case the system comprises an element for adjusting the polarization direction, the element for adjusting the polarization direction being that positioned between the light source and the splitter, such that the incident light at the splitter is polarized along the second direction.
the substrate has a surface intended to interact with the light source light, the surface being smooth.
the system further includes a sensor able to acquire an image of the objects.
the light from the light source forms a beam, the system including an optical system able to modify the size of the beam.
the objects are objects measuring less than a millimeter.
the objects are microorganisms.
the observation system further comprises a half-wave plate able to modify the polarization of light emitted by the light source.
the observation system further comprises a computer able to analyze the backscattered light detected by the detector to deduce at least one characteristic of the objects.
the observation system has no optics inserted between the splitter and the quarter-wave plate and between the quarter-wave plate and the substrate.
the objects are part of a Petri dish having a cylindrical body, the base surface of which is planar, and a cylindrical cover, the base surface of which is planar and forms an angle with the base surface of the body comprised between 0.1 degrees and 15 degrees.
the optic system is able to obtain a beam size comprised between 30 microns and 250 microns.

The description also describes a method for observing objects using a system for observing objects is proposed including a light source able to emit polarized light rectilinearly along a first direction, a holder able to receive a substrate having a surface including objects, at least one of the holder and the substrate being translucent or opaque, a detector able to collect the backscattered light from the interaction between the light emitted by light source and the objects, a polarization splitter able to reflect polarized light rectilinearly along a second polarization direction and able to transmit polarized light rectilinearly along a third direction, the second polarization direction being perpendicular to the third direction, and a quarter-wave plate. The method includes emitting polarized light rectilinearly along the first direction using a light source, the collection of the backscattered light from the interaction between the light emitted by the light source and the objects, reflecting the polarized light rectilinearly along the second polarization direction, and transmitting polarized light rectilinearly along the third direction.

According to specific embodiments, the method comprises one or more of the following features, considered alone or according to any technically possible combinations:
the light from the light source forms a beam, the system including an optical system able to modify the size of the beam.
the method includes adapting the size of the beam to the size of the objects.
the method includes locating an object in a large-field image.

BRIEF DESCRIPTION OF THE DRAWING FIGURES

Figure 2:
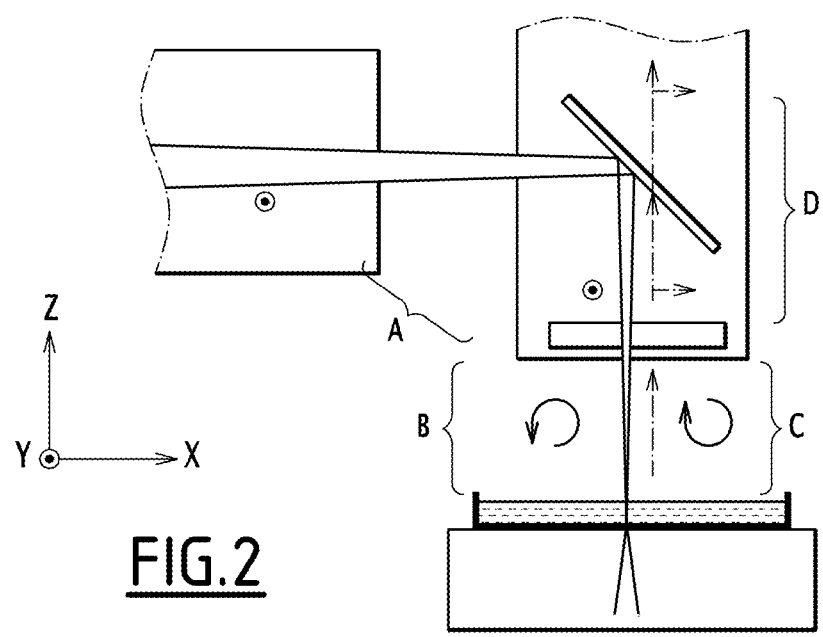
Figure 3:
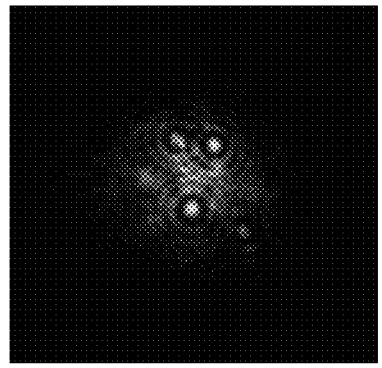
Figure 4:
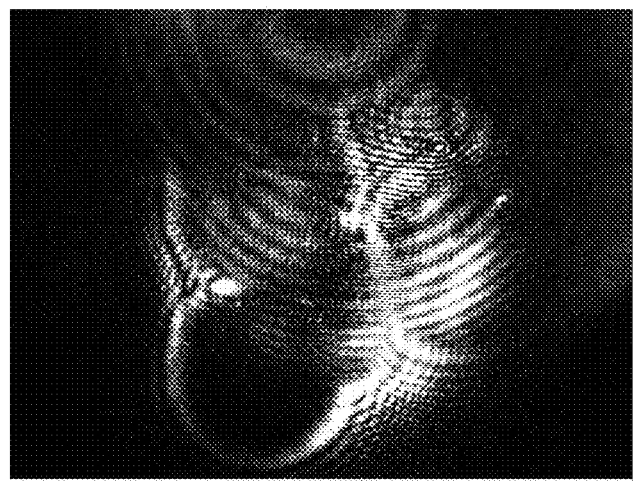
Figure 5:
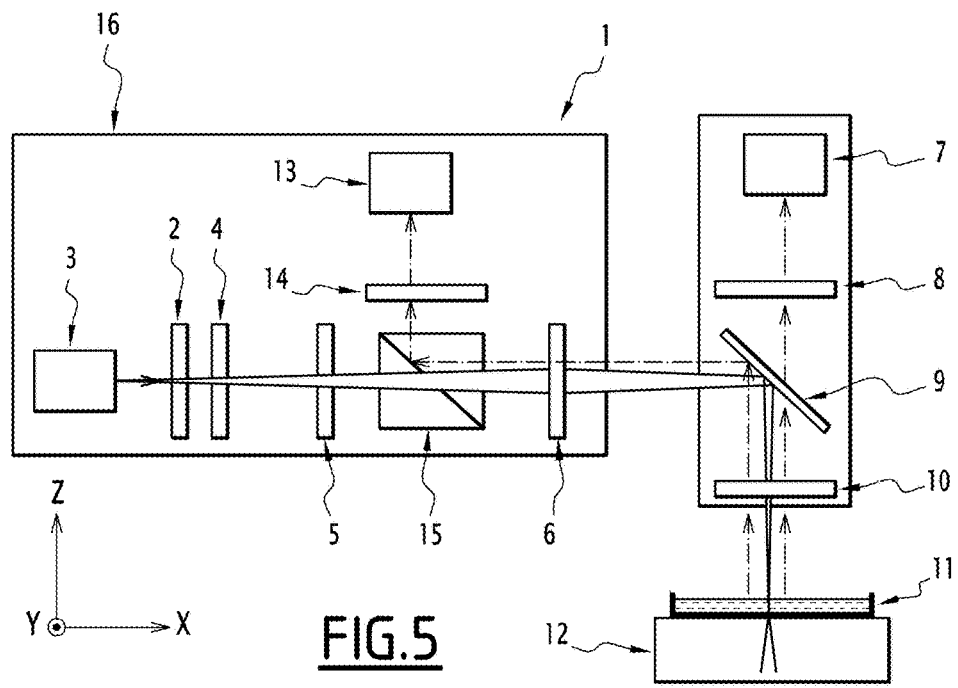
Figure 6:
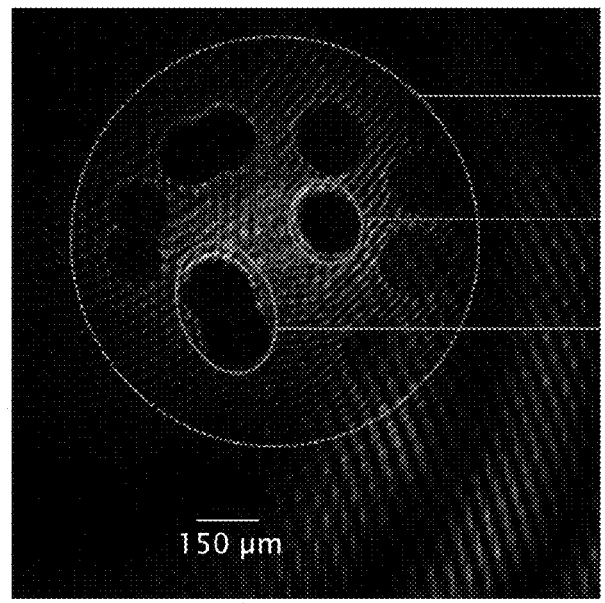
Figure 13:
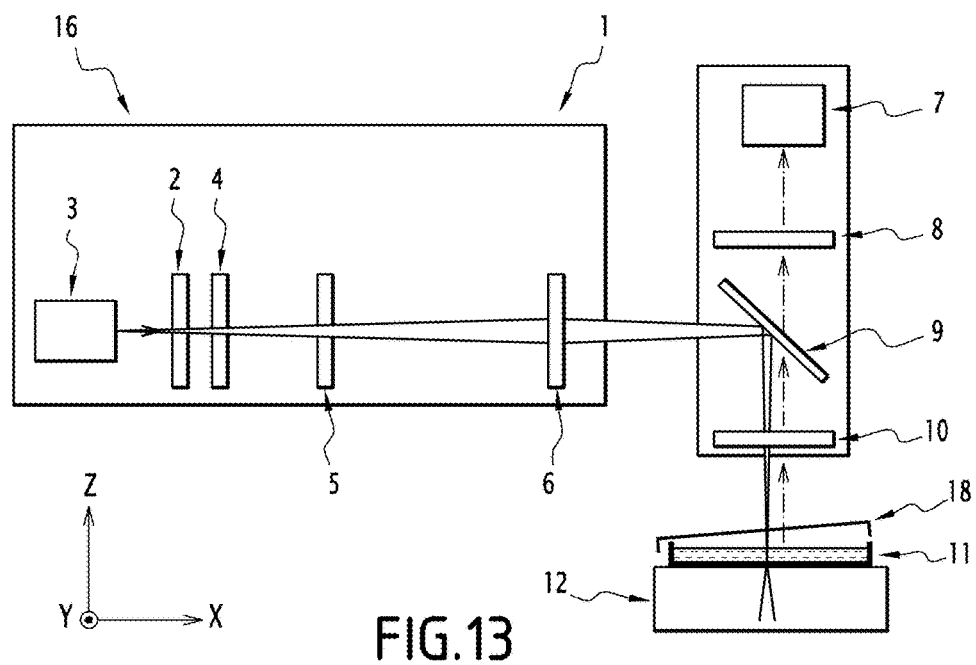
Figure 14:
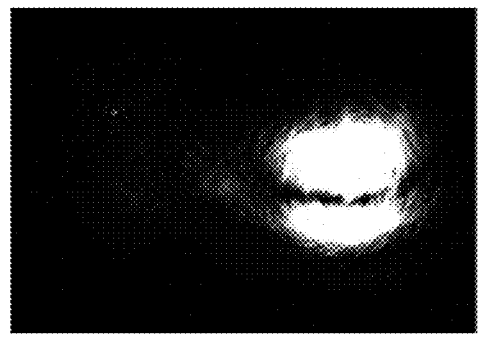
Figure 15:
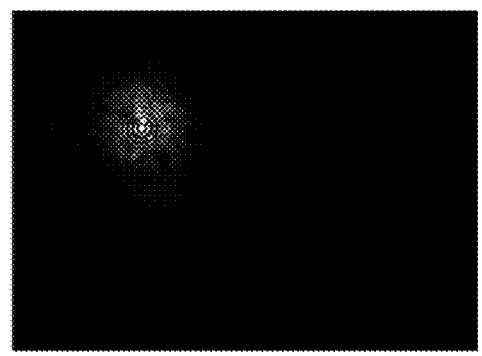

Other features and advantages of the invention will appear upon reading the following description of embodiments of the invention, provided as an example only and in reference to the drawings, which are:

FIG. 1, a schematic view of a first example observation system;

FIG. 2, an schematic view of a part of the system of FIG. 1 during operation;

FIG. 3, a diffraction pattern obtained using the system of FIG. 1 for 6 hours of growth of a bacteria micro-colony (*Escherichia coli* with ATCC number 11775) in a Petri dish;

FIG. 4, a diffraction pattern obtained using an observation system with no cube and quarter-wave plate for 6 hours of growth of a bacteria micro-colony (*Escherichia coli* with ATCC number 35421) in a Petri dish;

FIG. 5, a schematic view of a second example observation system;

FIG. 6, an image in the direct space obtained using the system of FIG. 5 for 6 hours of growth of a bacteria micro-colony (*Escherichia coli* with ATCC number 25922) in a Petri dish;

FIGS. 7 to 12, a set of images illustrating a procedure for aligning and adjusting the size of the probe beam on a bacteria colony for 6 hours of growth of a bacteria micro-colony (*Escherichia coli* with ATCC number 11775) in a Petri dish;

FIG. 13, a schematic view of a third example observation system;

FIG. 14, a diffraction pattern obtained using the system of FIG. 1 for 6 hours of growth of a bacteria micro-colony (*Escherichia coli* with ATCC number 25922) in a Petri dish when the cover of the Petri dish is laid flat, and FIG. 15, a diffraction pattern obtained using the system of FIG. 1 for 6 hours of growth of a bacteria micro-colony (*Escherichia coli* with ATCC number 25922) in a Petri dish when the cover of the Petri dish is inclined by 1 degree.

DETAILED DESCRIPTION OF THE INVENTION

A system for observing an object, called system 1, is shown in FIG. 1.

The system 1 makes it possible to observe a sample 11.

The sample 11 comprises a set of particles and a substrate holding the set of particles.

"Particles" refer to micrometric particles, for example cells, microorganisms. The microorganisms can, in particular bacteria, be able to be alongside one another, so as to form bacterial colonies, spores, fungi or yeasts. It is considered below that the set of particles is situated on the surface of a substrate.

Each particle has a maximal extension in one direction. Maximal extension means a characteristic size of the set of organisms. This for example is the diameter of the circle in which the set of organisms fits. In general, the invention applies to organisms or sets of organisms whose maximal extension is comprised between 100 nanometers (nm) and 1 millimeter (mm), preferably between 1 micrometer (µm) and 500 µm.

According to one particular embodiment, the system 1 is able to allow the observation of micrometric bacterial colonies, the characteristic size of which is smaller than 1 mm, for example comprised between 100 µm and 1 mm, or even between 50 µm and 500 µm. This allows an observation at an early stage of the development of the colonies. Time is then saved relative to methods based on the observation of millimetric bacterial colonies.

The system 1 also makes it possible to analyze a diffraction pattern. The analysis of the diffraction pattern makes it possible to ensure the counting, identification, sorting or monitoring of the observed particles. In particular, the identification of the particles can be done based on a comparison of each detected diffraction pattern with a library of reference diffraction patterns established beforehand.

The substrate can be capable of causing at least part of the set of organisms to grow. Thus, the substrate itself is a culture medium or is placed in contact with a culture medium.

According to one particular embodiment of the invention, the substrate is a solid substrate.

The solid substrate is for example an agar medium.

In the example of FIG. 1, the sample assumes the form of a Petri dish. A Petri dish has a cylindrical shape, the base surface of which is a circle. The base surface is planar. In the case at hand, the base surface is normal relative to the vertical of the location.

In the case of FIG. 1, the object to be observed is the surface of a blood agar measuring approximately 4-5 mm thick contained in a Petri dish with a diameter of 86 mm.

The system 1 includes a light source 3, a holder 12 for the sample 11, a detector 7, a lens 8, a polarization splitter 9 and a quarter-wave plate 10.

The light source 3 is able to emit spatially coherent light.

The light that the light source 3 is able to emit is also polarized rectilinearly along a first direction D1.

For example, the light source 3 is a laser source able to emit a laser beam. According to one alternative, the light source 3 is a light-emitting diode (LED).

The culture medium is placed in a chamber, the chamber itself being positioned on a holder 12.

The holder 12 is suitable for receiving a substrate having a surface suitable for the growth of objects.

The relative position of the holder 12 and the light source 3 can be adjustable so that the light emitted by the light source 3 interacts with objects having grown on the substrate.

At least one of the holder 12 and the substrate is opaque or translucent.

For example, the substrate may be opaque, translucent or transparent. When the substrate is transparent, the holder 12 is absorbent or diffusive, to avoid the reflection of the light on the holder 12.

The substrate can be made up of a transparent culture medium, to which an opacifying agent has been added. The opacifying agent can in particular be a mineral powder, of the kaolin type (white clay) or titanium dioxide, or an organic dye (methylene blue, phenol red, bromophenol blue, etc.).

The detector 7 is able to collect backscattered light from the interaction between the light emitted by the light source and the objects.

The lens 8 is infinity focused. This means that the detector 7 is positioned on its image focal point.

The expression "polarization splitter" refers to a device able to reflect polarization along a given direction and to transmit polarization along a perpendicular direction.

In the example of FIG. 1, the polarization splitter 9 is able to reflect polarized light rectilinearly along a second direction D2 and able to transmit polarized light rectilinearly along a third direction D3. The second direction D2 is perpendicular to the third direction D3.

According to the specific example of FIG. 1, the polarization splitter 9 is a plate.

In this example, the splitter 9 serves to transmit only one polarization direction and to reflect the other directions. The incident light in the beam is reflected by the splitter 9, while the light reflected by the sample 11 is transmitted.

According to another alternative that is not shown, the polarization splitter 9 is a cube.

The quarter-wave plate 10 is a phase delay plate of type λ/4.

The quarter-wave plate 10 has the property of transforming a rectilinear polarization into a circular polarization, and vice versa, i.e., a circular polarization into a rectilinear polarization.

The cube 9 and the quarter-wave plate 10 are arranged so that the cube 9 reflects the light emitted by the light source 3 toward the sample 11 and transmits the backscattered light from the interaction between the light emitted by the light source 3 and the objects toward the detector 7.

The operation of the system 1 will now be described.

The light source 3 emits light toward the splitter 9.

The light emitted by the light source 3 is incident on the splitter 9 with a polarization s.

The assembly of the splitter 9 and the quarter-wave plate 10 forms a device for selecting the polarization, the operation of which is explained in reference to FIG. 2.

The splitter 9 splits the polarizations. More specifically, according to the example of FIG. 1, the splitter 9 transmits the light whose polarization direction is parallel to the incidence plane, the incidence plane being a plane containing the incident ray and the normal to the considered face. The polarization direction parallel to the incidence plane is usually called polarization p.

The splitter 9 also reflects the light whose polarization direction is perpendicular to the incidence plane. The polarization direction perpendicular to the incidence plane is usually called polarization s.

When the incident light on the splitter 9 is polarized rectilinearly along a polarization s (part A in FIG. 2), the light emitted by the light source 3 is reflected toward the sample 11.

The light then propagates toward the quarter-wave plate 10.

The quarter-wave plate 10 converts the rectilinear polarization of the light into a left circular polarization.

The left circular polarized light then propagates toward the sample 11 (see part B in FIG. 2).

The light is then backscattered by the sample 11.

A change of polarization direction then occurs due to a property of the circularly polarized light upon reflection on an interface. Indeed, upon reflection on an interface, the polarization direction of a circularly polarized light changes directions. Thus, after reflection, a straight circular polarization light beam has a left circular polarization.

The backscattered light is therefore polarized with a circular polarization in the direction opposite the incident circular polarization, i.e., right circular polarized (see part C in FIG. 2).

The quarter-wave plate 10 then converts the right circular polarization of the light into a straight polarization of type p.

The rectilinear polarized light of type p then propagates toward the splitter 9 (see part D in FIG. 2).

The splitter 9 transmits the light with polarization p such that the light propagates toward the lens 8.

The lens 8 serves to form, on the detector 7, an image of the interferences, which are localized to infinity.

The light then propagates toward the detector 7.

The detector 7 then records a diffraction pattern corresponding to the elastic diffusion of the photons by the objects.

According to one alternative, the splitter 9 transmits the light emitted by the light source, toward the sample 11, and reflects the backscattered light, the polarization direction of which is D3, toward the detector 7.

In general, the splitter 9 is able to direct the incident light, coming from the light source, toward the sample 11. It is also able to direct the light backscattered by the sample 11, the polarization direction of which is perpendicular to that of said incident light, toward the detector 7. The term "direct" then refers to transmitting or reflecting the light.

One example diffraction pattern obtained for 6 hours of growth of bacteria in a Petri dish is shown in FIG. 3. In the case at hand, the substrate is a sheep's blood agar COS. The acronym COS stands for "Columbia Blood Sheep".

As a comparison, the same diffraction pattern is shown in FIG. 4 for a system with no cube and quarter-wave plate. An unusable diffraction pattern is observed.

The differences observed between FIGS. 3 and 4 can be explained by the fact that the management of the polarization proposed for the system 1 makes it possible to eliminate all stray reflections caused by the surfaces of the optics on the path of the beam emitted by the light source 3 and the back-reflected beams.

It has been observed that the diffraction pattern obtained with the system 1 is more easily usable. As a result, the system 1 makes it possible to observe diffraction patterns formed by particles localized on an opaque substrate or on a substrate placed on an opaque holder.

According to this example, rapid bacterial micro-colony identifications, on the surface of an opaque medium, in particular in only 6 hours of culture, are possible using the system 1.

The system 1 is also useful for macro-colonies, and more generally, for any type of particle as previously defined.

Furthermore, the system 1 allows a direct measurement on the substrate on which the object rests, in particular when the substrate is a culture medium placed in a chamber of the Petri dish type. This is simpler than the microscopic techniques involving transferring objects onto a compatible substrate with a transmission measurement.

Another application is the detection of molds on an opaque substrate.

Preferably, the substrate is a smooth enough culture medium to avoid the modification of reflections or back scattering on the surface of the substrate, which generates noise in the image that is detrimental to the quality of the measurement. "Smooth" refers to a roughness preferably of less than 100 µm rms ("root mean square"), better 50 µm at least locally, near a particle to be detected.

According to one embodiment, the only component between the splitter 9 and the sample 11 is the quarter-wave plate 10.

This means that no other optical component is inserted between the splitter 9 and the sample 11.

This makes it possible to increase the quality of the images while avoiding the generation of stray reflections caused by optical systems, for example, lenses or objectives, positioned between the splitter 9 and the sample 11.

According to one embodiment, the beam shaping components are positioned upstream from the splitter 9.

The terms "upstream" and "downstream" are defined relative to the direction of propagation of the light. Thus, the beam shaping components are positioned upstream from the splitter 9 when the components are positioned between the light source 3 and the first face of the splitter 9.

This makes it possible to improve the quality of the obtained diffraction images.

According to one embodiment, the quarter-wave plate 10 is treated against glare.

This makes it possible to avoid stray reflections on the quarter-wave plate 10.

Advantageously, the first direction D1 and the second direction D2 are identical.

To modify the first direction D1, it is possible to consider turning the light source 3 around its optical axis or inserting a half-wave plate able to rotate around its axis of revolution. The half-wave plate then serves to adjust the polarization of the beam emitted by the light source 3, such that the incident beam at the splitter 9 is polarized rectilinearly along the second direction D2. Naturally, such a plate, acting as element to adjust the polarization direction, is not necessary if the beam emitted directly by the light source is directly polarized rectilinearly along the second direction D2.

According to the embodiments, the half-wave adjustment plate may or may not be part of the light source 3. A half-wave plate belonging to the light source 3 has the advantage of not being cumbersome and already being positioned on the frame.

According to one embodiment, the system 1 further includes a computer.

The computer is for example suitable for comparing diffraction patterns acquired by the detector 7 and determining at least one characteristic relative to the set of particles from the results of the comparison.

According to one embodiment, the sample 11 is part of the system 1.

Alternatively, the substrate is able to vary the optical index of at least part of the particles of the set of particles. This makes it possible to increase the differences between the different diffraction patterns.

Thus, as an example, the substrate includes precipitant chromogenic substrates.

A second example system 1 is shown in FIG. 5.

Subsequently, a vertical direction and two transverse directions are defined. Each of these directions is symbolized by axes shown in FIG. 5, namely the axis Z for the vertical direction, the axis X for the first transverse direction and the axis Y for the second transverse direction.

Like for the system 1 according to the first example, the system 1 illustrated in FIG. 5 comprises the light source 3, the holder 12, the detector 7, the polarization splitter cube 9 and the quarter-wave plate 10.

The system 1 of FIG. 5 also includes an optical density 2, a half-wave plate 4, a first lens 5, a splitter plate 15, a second lens 6, a third lens 8, a fourth lens 14, a sensor 13 and a first translation 16.

The optical density 2 makes it possible to attenuate the optical power coming out of the light source 3.

The optical density 2 is, according to the example of FIG. 5, an optical density neutral density filter 4.

According to the specific example, the light source 3 is a monochromatic laser source emitting at a wavelength of 532.2 nanometers (nm).

Preferably, the light source 3 emits in a wavelength range comprised between 250 nm and 1200 nm. In general, the wavelength must be smaller than the maximal extension of the observed object, while allowing the use of standard detection means. The wavelengths in the visible or near infrared domain are then preferred. Alternatively, the wavelength of the laser beam is in a different wavelength band. The wavelength in particular depends on the organism to be observed and its sensitivity to illumination by a laser beam.

The obtained laser beam has a diameter of 0.334 millimeters and a divergence of 2.07 mrad.

The laser beam is single-mode (TEM00) and polarized rectilinearly.

The laser beam has a power of 20.1 milliWatts (MW).

The combination of the first lens 5 and the second lens 6 makes it possible to shape the beam from the light source 3 in order to obtain a range of beam sizes comprised between 30 microns and 250 microns (i.e., greater than or equal to 30 microns or less than or equal to 250 microns).

The first lens 5 is, according to the example of FIG. 5, a biconcave lens with focal −20 mm.

According to the example of FIG. 5, the second lens 6 is a biconvex lens with focal +75.0 mm having undergone an anti-glare treatment for the wavelength range of 400 nm-700 nm.

The splitter plate 15 makes it possible to separate an incident beam into two beams.

In the case at hand, the splitter plate 15 makes it possible send part of the light toward the splitter 9 and another part toward the sensor 13.

According to the example of FIG. 5, the detector 7 is a camera of the CMOS type (CMOS standing for Complementary Metal Oxide Semiconductor).

According to another alternative, the detector 7 is a CCD camera (acronym for Charge-Coupled Device).

The third lens 8 makes it possible to collect the backscattered light and focus it toward the detector 7, as previously described.

According to the second example, the third lens 8 is a biconvex lens with focal +40.0 mm having undergone an anti-glare treatment for the wavelength range of 400 nm-700 nm.

According to the illustrated example, the splitter 9 is able to interact with waves whose wavelength is comprised between 420 nm and 680 nm.

The fourth lens 14 makes it possible to collect the light from the substrate in the direct space and focus it toward the sensor 13.

According to the example of FIG. 5, the fourth lens 14 is a convex-plane lens with focal +150.0 mm having undergone an anti-glare treatment for the wavelength range of 350 nm-700 nm.

The holder 12 includes second transmission means allowing movement of the sample in two directions, i.e., the first longitudinal direction X and the second longitudinal direction Y.

The sensor 13 makes it possible to image the sample 11 in direct space at the same time as viewing the beam emitted by the light source 3.

The sensor 13 is for example a camera of the CMOS type (CMOS standing for Complementary Metal Oxide Semiconductor).

The first translation 16 allows the set of elements of the light source 3, the optical density 2 and the first and second lenses 5 and 6 to move along the first transverse direction X.

The movement of the first translation 16 contributes to varying the size of the beam on the object between 30 microns and 1 millimeter.

As an example, the maximal travel of the first translation 16 is comprised between 150 mm and 200 mm, with a precision of 1 micron.

The operation of the system 1 according to the second example is similar to the operation of the system 1 according to the first example.

The system 1 also makes it possible to obtain images in direct space of the sample 11 via the sensor 13.

The sensor 13 makes it possible to have an indication of the size of the micro-colonies and their shape.

As an illustration, it is assumed that a micro-colony requires imaging.

First, the micro-colony is localized on a large-field image. In the proposed context, a large-field image corresponds to a position far from the waist of the beam. One example of such a figure is shown in FIG. 6. In this figure, there are several micro-colonies in the circle in dotted lines. One micro-colony is surrounded by a first circular outline. A second oval outline surrounds two overlapping colonies.

The micro-colonies appear in the form of shadows on the sensor 13, since the light beam penetrates the agar, then is backscattered. The dark spots correspond to the absorption of all or part of the backscattered light, by the particles present on the surface of the substrate. The diffusion in the substrate results in depolarizing the light. Thus, part of the light backscattered by the substrate is depolarized and is not transmitted through the splitter 9 toward the detector 7. This part of the backscattered light is reflected toward the splitter plate 15, the splitter plate 15 directing it toward the sensor 13.

The image provided by the sensor 13 is a control image, providing an overview of the examined particles. Such a control image makes it possible to ensure that particles are indeed present in the observed field. The control image also makes it possible to detect the presence of overlapping particles, in particular when the particles are micro-colonies. Such overlaps lead to the observation of deformed diffraction patterns, and can be detrimental in applications where each diffraction pattern is used for identification purposes.

The control image can also allow a rough centering of the incident beam relative to the particles to be examined.

At the end of this step, the image produced by the detector 7 is observed. The produced image has one or a plurality of elementary diffraction patterns, each elementary diffraction pattern corresponding to a particle or a clump of particles.

The beam is then gradually aligned on the micro-colony until an optimal interference pattern is obtained in terms of number of fringes and contrast of the fringes. The expression "alignment" refers to a movement of the sample 11, relative to the incident beam, in at least one of the three directions, i.e., the first transverse direction X, the second transverse direction Y and the axis Z.

FIGS. 7 to 12 are a set of images obtained by the detector 7 illustrating such a procedure for aligning and adjusting the size of the probe beam on a bacteria colony for 6 hours of growth of the bacteria in a Petri dish.

FIG. 7 shows a large-field image in which it is possible to see three micro-colonies. FIG. 8 shows that the beam is slightly offset relative to the micro-colony to be imaged. FIG. 9 corresponds to the case where the beam is centered relative to the micro-colony to be imaged.

For implementation, for example, the two translations 16 and 12 are used while controlling the symmetry of the diffraction pattern acquired on the detector 7. Such a control is manual or automatic, for example by using mathematical tools such as a Hough transform intended to detect circles.

FIG. 10 illustrates the case where the beam has a size in the plane of the sample 11 that is smaller than the micro-colony. It is observed that the interference pattern is extinguished. As a result, the size of the beam is gradually increased (see FIG. 11). The increase is for example done by moving the first translation with pitches of 100 microns to 500 microns. The gradual increase is done until reaching an optimal pattern, i.e., a pattern having a maximum of contrasting rings. FIG. 12 illustrates such a pattern. The determination of the optimal pattern is done by the operators eye, or by image processing.

The proposed procedure makes it possible to adapt the size of the beam to the size of the micro-colonies.

Thus, the system 1 makes it possible to perform the measurement on objects with different sizes, from 1 micron to 500 microns, owing to a unique and simple architecture providing access to a range of appropriate beam sizes.

The system 1 thus makes it possible to detect and localize the micrometric objects in a large field of view. This localization is done upstream from the measurement of the interference image by reflection; this makes the measurement easier and faster.

A third example system 1 is shown in FIG. 13.

The third example system 1 is similar to the second example system 1. The remarks applying to the shared elements are therefore also valid for the third example system 1. These remarks are not repeated. Only the differences are shown.

Unlike the system 1 according to FIG. 5, the third example system 1 does not include a splitter plate, fourth lens and sensor.

The sample 11 of the previous examples is comprised in a chamber of the Petri dish type with no cover.

Conversely, the chamber of the sample 11 of FIG. 13 has a cover 18. This makes it possible to avoid cross-contamination (i.e., contamination of the outside medium crossed with contamination of the substrate, which leads to contamination of the dishes by dishes previously used). This also makes it possible to avoid operator contamination. In such a situation, the cover 18 is preferably transparent.

The cover 18 has an angle relative to the horizontal. According to the example of FIG. 13, this angle is 1 degree.

The comparison of FIGS. 14 and 15 makes it possible to show the interest of such a configuration. Indeed, FIG. 14 is a diffraction pattern obtained for 6 hours of growth of a bacterium in a Petri dish when the cover of the Petri dish is placed flat, while FIG. 15 is a diffraction pattern obtained for 6 hours of growth of a bacterium in a Petri dish when the cover of the Petri dish is inclined by 1 degree. The diffraction pattern is of better quality in terms of contrast of the fringes in the case of FIG. 15.

More generally, the stray reflections from the cover of the dish can be eliminated by inclining the cover 18 by several degrees relative to the horizontal, for example between 0.1° and 15°, preferably between 1° and 5°.

In other words, the base surface of the cover 18, which is cylindrical, forms an angle with the base surface of the body of the Petri dish. This angle is comprised between 0.5° and 5°.

In all of the described embodiments, the system 1 allows the identification of bacterial colonies on opaque nutritional mediums by elastic diffusion with reflection geometry. In particular, it becomes possible to use a substrate that is a blood agar.

In other words, the system 1 allows the acquisition of interference patterns resulting from the reflection of a light beam on microorganisms (single bacteria, micro-colonies, macro-colonies) and on micrometric objects resting on opaque substrates. These substrates do not allow measurement in transmission, as is done by the current devices. The system 1 therefore makes it possible to expand the field of application to opaque substrates by proposing a nondestructive, automatable and rapid method.

It has also been shown that the system 1 makes it possible to resolve several difficulties. In particular, the system 1 allows quick localization of all of the micro-colonies present in the Petri dish (the diameter of which is 86 mm). The system 1 also makes it possible to adapt the size of beam of the light source 3 to the size of the micro-colonies, the sizes being able to vary, depending on the bacterial species, between 30 microns and 250 microns. The size can also vary by several tens of microns for a same species and a same culture. The adaptation can be done within a series of measurements done on a same dish. The system 1 also makes it possible to center the beam from the light source 3 on the micro-colony or -colonies in question. The system 1 is also able to acquire the interference patterns from the reflection of the probe beam on the studied micro-colony or -colonies. The system 1 also makes it possible to calculate parameters characterizing the interference patterns and compare the parameters to an existing base. Such a possibility opens the way for learning techniques, and in particular supervised techniques of the SVM (Support Vector Machine) type.

Other alternatives of the system 1, not illustrated, can be considered, provided that the characteristics are compatible. Typically, according to one embodiment that is not illustrated, the system 1 is according to the third example and includes a sensor 13.

To illustrate the capacities of the system 1, below, three specific experiments conducted with the preceding system 1 are outlined.

In these experiments, the bacterial strains are commercial ATCC (American Type Culture Collection) strains. From a culture in liquid medium after 24 h of incubation at 37° C., a suspension is taken of 5 milliliters (ml) comprising water and a quantity of cells from the strain such that the turbidity of the solution is equal to 0.5 McF (McFarland standard). The suspension is diluted by a factor of 1/1000 to 1/100 depending on the strains. Next, a volume of 10 µL of the suspension is next inoculated on the COS culture medium contained in a chamber of the Petri dish type. The dish thus inoculated is incubated at 37° C. The dish is removed from the incubator 6 h after inoculation.

After the method described above, reflection interference images are obtained on the colonies. Preferably, each image includes only one interference pattern, which corresponds to a microorganism to be characterized.

Each image is then projected on a Zernike moments base taken from the family of orthogonal Zernike polynomials defined in polar coordinates on the unit disc. Such a base offers the advantage of invariance by rotation and a limitation of the redundancy of the information. Such a projection is known in itself. This step makes it possible to have scalar indicators relative to the interference pattern comprised in the image. Other quantitative analysis methods can be used, which consist of projecting an image in a base, in order to obtain coordinates of the analyzed image in this base.

A vector, gathering said indicators, called descriptor, is obtained for each image. Such a vector is made up of 120 components corresponding to the modules of the components of the projection over the first 120 polynomials of the base.

Once this database is established, a classification algorithm is used of the support vector machine (SVM) type, and more particularly the sequential minimum optimization (SMO) algorithm. Indeed, training a support vector machine requires solving a large quadratic optimization problem, and the SMO logarithm proposes to reduce the computing time by dividing it into the smallest possible quadratic optimization problems, which will be solved analytically. This classification is next evaluated by a cross-validation step (also called "10-fold cross-validation"). The results are then combined in the form of a confusion matrix.

For a first experiment, 400 samples equally divided among 4 strains of the same *Escherichia Coli* species are studied. The obtained confusion matrix is as follows:

TABLE 1

Confusion matrix for the first experiment

| Strain of *Escherichia Coli* | Classified EC10 | Classified EC21 | Classified EC28 | Classified EC11 |
|---|---|---|---|---|
| EC10-ATCC 25922 | 96 | 1 | 1 | 2 |
| EC21-ATCC 35421 | 7 | 80 | 4 | 9 |
| EC28-ATCC11775 | 6 | 6 | 80 | 8 |
| EC 11-ATCC 8739 | 5 | 4 | 2 | 89 |

The confusion matrix of table 1 reads as follows: taking the line across from strain EC10, out of 100 descriptors of EC10, 96 were recognized as being EC10, 1 as being ED21, 1 as being EC28 and 2 as being EC11, and so forth. By applying this to each species, out of 400 descriptors, 345 were correctly recognized, and 55 were confused with the descriptors of another strain. This corresponds to a global classification rate of more than 86%.

Table 1 thus corresponds to a classification over 4 strains of the same species: *Escherichia coli*. This corresponds to a much finer level of identification than inter-species identification. A very satisfactory global classification rate is obtained of more than 80% (86.25%, to be exact). This rate is of the same order of magnitude as the results that are obtained with diffraction patterns in transmission.

For a second experiment, 500 samples equally divided among 5 species of bacteria are studied. The obtained confusion matrix is as follows:

TABLE 2

Confusion matrix for the second experiment

| Strain (species) | Classified EC21 | Classified EC8 | Classified AB30 | Classified CF7 | Classified SE9 |
|---|---|---|---|---|---|
| EC21-ATCC 35421 (*Escherichia coli*) | 89 | 8 | 0 | 1 | 2 |
| EC10-ATCC 25922 (*Enterobacter cloacae*) | 2 | 70 | 6 | 0 | 22 |
| AB30-ATCC 23220 (*Acinetobacter baumanii*) | 2 | 4 | 94 | 0 | 0 |
| CF7-ATCC 8090 (*Citrobacter freundii*) | 1 | 0 | 0 | 98 | 1 |
| SE9-ATCC 14990 (*Staphylococcus epidermidis*) | 0 | 14 | 0 | 0 | 86 |

In the second experiment, the global classification rate is more than 87%. This rate is of the same order of magnitude as the results that are obtained with diffraction patterns in transmission.

For a third experiment, 300 samples equally divided among 3 species of the same genus of Candida fungus are studied. The obtained confusion matrix is as follows:

TABLE 3

Confusion matrix for the third experiment

| Strain (species) | Classified EC10 | Classified EC21 | Classified EC28 |
|---|---|---|---|
| CA36-ATCC 14053 (*Candida albicans*) | 88 | 0 | 10 |
| CG38-ATCC 2001 (*Candida glabrata*) | 0 | 100 | 0 |
| CT37-ATCC 13803 (*Candida tropicalis*). | 6 | 0 | 94 |

In the third experiment, the global classification rate is 94%. The implemented method makes it possible to obtain diffraction patterns usable by analysis and classification algorithms, in order to establish assistance in identifying microorganisms.

The invention claimed is:

1. A system for observing objects on a substrate, comprising:
    a light source that emits polarized light rectilinearly along a first direction,
    a holder that receives said substrate having a surface and comprising objects, at least one of the holder and the substrate being translucent or opaque,
    a detector that collects the backscattered light from the interaction between the light emitted by light source and the objects,
    a polarization splitter that reflects polarized light rectilinearly along a second polarization direction and transmits polarized light rectilinearly along a third direction, the second polarization direction being perpendicular to the third direction, and
    a quarter-wave plate,
    wherein, the polarization splitter and the quarter-wave plate are arranged so that the polarization splitter directs the light emitted by the light source toward the substrate through the quarter-wave plate, and directs the backscattered light from the interaction between the light emitted by the light source and the objects through the quarter-wave plate toward the detector, and
    wherein the light from the light source forms a beam, the system comprising an optical system that modifies the size of the beam.

2. The system for observing objects according to claim 1, wherein the objects are microorganisms, and the substrate is a solid substrate.

3. The method according to claim 2, wherein the substrate is an agar substrate.

4. The system for observing objects according to claim 1, wherein:
    either the first direction and the second direction are identical;
    or the first direction is different from the second direction, in which case the system comprises an element for adjusting the polarization direction, the element for adjusting the polarization direction being that positioned between the light source and the splitter, such that the incident light at the splitter is polarized along the second direction.

5. The system for observing objects according to claim 1, wherein the substrate has a surface intended to interact with the light source light, the surface being smooth.

6. The system for observing objects according to claim 1, wherein the system further includes a sensor that acquires an image of the objects.

7. The system for observing objects according to claim 1, wherein the optic system obtains a beam size comprised between 30 microns and 250 microns.

8. The system for observing objects according to claim 1, wherein the objects are objects measuring less than a millimeter.

9. The system for observing objects according to claim 1, wherein the objects are microorganisms.

10. The system for observing objects according to claim 1, wherein the observation system further comprises a half-wave plate that modifies the polarization of light emitted by the light source.

11. The system for observing objects according to claim 1, wherein the observation system further comprises a computer that analyzes the backscattered light detected by the detector to deduce at least one characteristic of the objects.

12. The system for observing objects according to claim 1, wherein the observation system has no optics inserted between the polarization splitter and the quarter-wave plate and between the quarter-wave plate and the substrate.

13. The system for observing objects according to claim 1, wherein the objects are part of a Petri dish having a cylindrical body, the base surface of which is planar, and a cylindrical cover, the base surface of which is planar and forms an angle with the base surface of the body comprised between 0.1 degrees and 15 degrees.

14. A method for observing objects using a system for observing objects, comprising:
    a light source that emits polarized light rectilinearly along a first direction,
    a holder that receives a substrate having a surface including objects, at least one of the holder and the substrate being translucent or opaque,
    a detector that collects the backscattered light from the interaction between the light emitted by light source and the objects,
    a polarization splitter that reflects polarized light rectilinearly along a second polarization direction and transmits polarized light rectilinearly along a third direction, the second polarization direction being perpendicular to the third direction, and
    a quarter-wave plate,
    wherein the polarization splitter and the quarter-wave plate are arranged so that the polarization splitter directs the light emitted by the light source toward the substrate through the quarter-wave plate, and directs the backscattered light from the interaction between the light emitted by the light source and the objects through the quarter-wave plate, toward the detector,
    wherein the light from the light source forms a beam, the system comprising an optical system that modifies the size of the beam,
    wherein the method comprises:
    emitting polarized light rectilinearly along a first direction via a light source,
    collecting the backscattered light from the interaction between the light emitted by light source and the objects,
    reflecting the polarized light rectilinearly along the second polarization direction, and
    transmitting the polarized light rectilinearly along the third direction.

15. The method according to claim 14, wherein the method further comprises adapting the size of the beam to the size of the objects.

16. The method according to claim 14, wherein the method further comprises locating an object in a large-field image.

\* \* \* \* \*